United States Patent [19]

Lipovsek et al.

[11] Patent Number: 4,736,738
[45] Date of Patent: Apr. 12, 1988

[54] INSTRUMENT KIT AND PROCEDURE FOR PERFORMING POSTERIOR LUMBAR INTERBODY FUSION

[76] Inventors: Matej Lipovsek, Splosna bolnisnica, Ljubljanska 5, 62000, Maribor; Joze Globevnik, Regentova 12,, Maribor 62000, both of Yugoslavia

[21] Appl. No.: 729,648

[22] Filed: May 2, 1985

[30] Foreign Application Priority Data

Jul. 9, 1984 [YU] Yugoslavia .................... 1203/84

[51] Int. Cl.[4] ............................................. A61F 5/04
[52] U.S. Cl. ............................ 128/92 V; 128/92 YJ; 128/92 VT
[58] Field of Search ............... 128/92 E, 303 R, 305, 128/92 X

[56] References Cited

U.S. PATENT DOCUMENTS

| 2,543,780 | 3/1951 | Hipps et al. | 128/92 E |
| 3,716,057 | 2/1973 | Rubin | 128/305 |
| 4,150,675 | 4/1979 | Comparetto | 128/92 E |
| 4,324,044 | 4/1982 | Shahinian, Jr. | 128/305 |
| 4,349,058 | 9/1982 | Comparetto | 128/305 |
| 4,539,976 | 9/1985 | Sharpe | 128/305 |
| 4,545,374 | 10/1985 | Jacobson | 128/305 |
| 4,557,259 | 12/1985 | Wu | 128/92 E |
| 4,559,936 | 12/1985 | Hill | 128/92 E |

Primary Examiner—C. Fred Rosenbaum
Assistant Examiner—C. W. Shedd
Attorney, Agent, or Firm—Leonard Bloom

[57] ABSTRACT

Instrument kit and method for performing posterior lumbar interbody fusion. The surgical procedure is done through the spinal canal rather than outside the spinal canal as has been done previously. The posterior lumbar interbody fusion procedure is faster, simpler, less bloody and less expensive than prior art vertebrae fusion procedures. The surgical procedure of this invention is carried out using a novel instrument kit comprising first and second shafts, first and second chisels, a retaining ring with set screw, an extraction hammer, a tamper, and a hook.

18 Claims, 9 Drawing Sheets

INSTRUMENT KIT AND PROCEDURE FOR PERFORMING POSTERIOR LUMBAR INTERBODY FUSION

FIELD OF THE INVENTION

This invention is concerned with an instrument kit and a procedure for performing posterior lumbar interbody fusion, or vertebrae fusion.

BACKGROUND OF THE INVENTION

Posterior lumbar interbody fusion, or vertebrae fusion, is a relatively common surgical procedure. Vertebrae fusion operations using traditional surgery are done outside the spinal canal and take about 3.5 to 4 hours to perform. However, the prior art procedure has a number of deficiencies. For example, a separate incision, usually in the pelvis, is required to obtain bone grafts. Posterior lumbar interbody fusions performed using traditional surgery have a success rate of about 78% and are expensive, costing the patient about $10,000.

SUMMARY OF THE INVENTION

I have invented an improved surgical procedure for performing posterior lumbar interbody fusions and an instrument kit for performing the surgery.

In contrast to traditional surgery, our procedure is done through the spinal canal rather than outside. Our procedure takes about 2 hours in contrast to the 3.5 to 4 hours of prior art procedures, is less bloody, and does not require a cast. Moreover our procedure typically uses bone cut from the spine during laminectomy for grafts rather than requiring a separate incision to obtain bone grafts from the pelvis as is the case with traditional surgery. Moreover, posterior lumbar interbody fusions performed by the procedure of this invention have a success rate of about 88% compared to the approximately 78% success rate of traditional procedures. Finally, our procedure is less expensive for the patient, costing about half as much as a procedure using traditional surgery.

In the practice of our invention, a laminectomy is performed whereby lamina are cut with bone cutters at two levels along the spinous process. In cases of bilateral fusion, lamine are cut at two levels along the spinous process on each side. The lamina are used as bone grafts.

Next, the degenerative disk material is removed from between the vertebrae to be fused. Then, using the instruments of this invention, a groove is cut into the lower edge of the upper vertebral body. A similar groove is cut into the upper edge of the lower vertebral body so that the grooves in the upper and lower vertebral bodies line up. A bone graft is then wedged into the grooves to thereby fuse the upper and lower vertebrae together. The wound is then closed by suturing lumbar muscles and fascia.

Accordingly, it is an object of this invention to provide an improved surgical procedure for performing posterior lumbar interbody fusions.

It is another object of this invention to provide an instrument kit for performing the posterior lumbar interbody fusion procedure of this invention.

It is yet another object of this invention to provide an instrument kit and surgical procedure for performing posterior lumbar interbody fusions more quickly and economically than is possible by using traditional surgical techniques.

The foregoing and other objects are accomplished by the practice of this invention. Broadly viewed in one of its principal aspects, this invention constitutes a process for performing a posterior lumbar interbody fusion comprising the following steps:

1. Removing lamina from the two vertebrae to be fused;
2. Cleaning and shaping said lamina for subsequent use as bone grafts;
3. Removing degenerative disk material from between the vertebrae to be fused;
4. Cutting a groove into the lower edge of the upper vertebral body to be fused;
5. Cutting a groove into the upper edge of the lower vertebral body to be fused, said groove being in line with the groove in said upper vertebral body, and
6. Wedging a bone graft into the grooves to thereby fuse said upper and lower vertebrae.

The foregoing surgical procedure is carried out using an instrument kit comprising a first shaft, a second shaft, a first chisel, a second chisel, a retaining ring with a set screw, an extraction hammer, a tamper, and a hook.

The present invention constitutes an improved surgical procedure for performing posterior lumbar interbody fusions and an instrument kit for performing the surgical procedure. The surgical procedure is characterized by being faster, less bloody, less expensive and more often successful than traditional surgical procedures. The instrument kit provides surgical instruments that are specifically adapted for use in the procedure of this invention.

The nature and substance of the present invention as well as its objects and advantages will be more clearly perceived and fully understood by referring to the following description and claims taken in connection with the accompanying drawings which are described briefly below.

DESCRIPTION OF THE PREFERRED EMBODIMENTS

The instrument kit and method for performing posterior lumbar interbody fusions in accordance with this invention significantly advance the art. The surgical procedure of this invention has a number of advantages over traditional procedures in that it is faster, simpler, less bloody, less expensive for the patient, and has a higher success rate. The surgical procedure of this invention is carried out using a novel set of instruments that are specifically adapted for use in the procedure.

Figure 1:
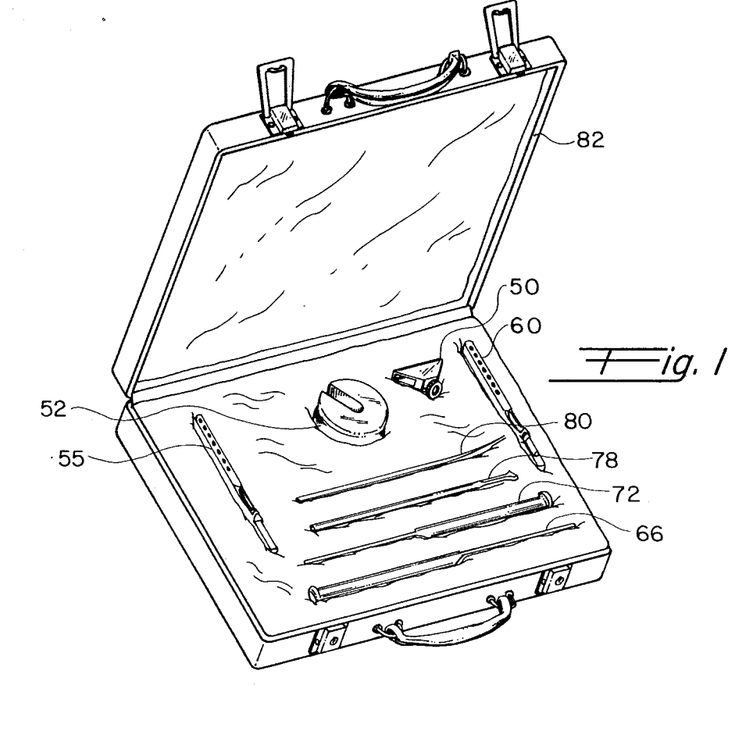
FIG. 1 is a perspective view of the instrument kit of the invention in a carrying case.
Figure 2:
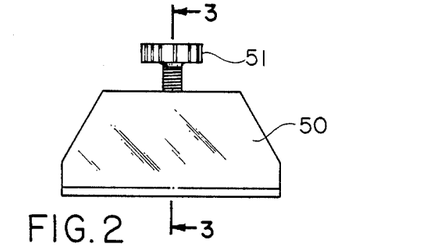
FIG. 2 is a side elevation of the retaining ring and set screw.
Figure 3:
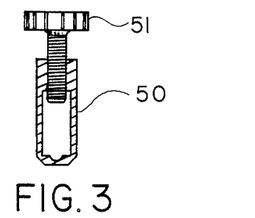
FIG. 3 is a sectional view of the retaining ring and set screw, taken along the lines 3—3 of FIG. 2.
Figure 4:
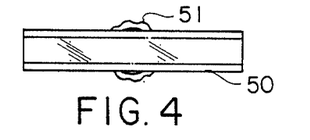
FIG. 4 is a bottom plan of the retaining ring and set screw.
Figure 5:
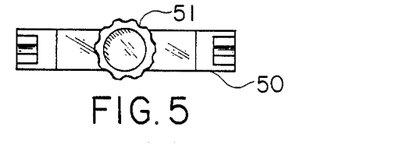
FIG. 5 is a top plan of the retaining ring and set screw.

FIG. 1 is a perspective view of the instruments of this invention in carrying case 82.

There are eight instruments in the kit used in the surgical procedure of this invention. Each instrument is a precision part made from high-quality steel used for medical and surgical purposes.

FIGS. 2, 3, 4, and 5 show side elevation, sectional, bottom plan and top plan, respectively, of retaining ring 50 and set screw 51.

Figure 6:
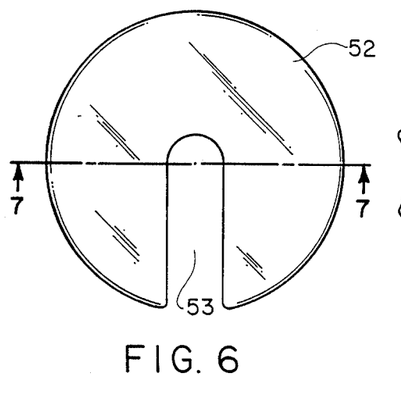
FIG. 6 is a top plan of the extraction hammer.
Figure 7:
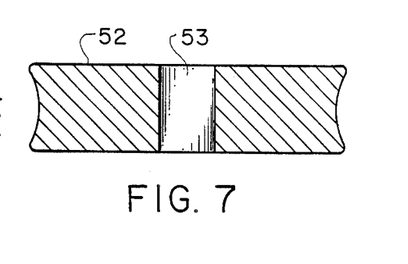
FIG. 7 is a sectional view of the extraction hammer, taken along the lines 7—7 of FIG. 6.
Figure 8:
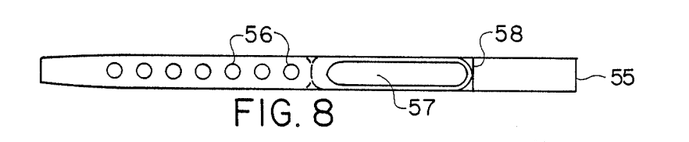
FIG. 8 is a top plan of the first shaft.
Figure 9:
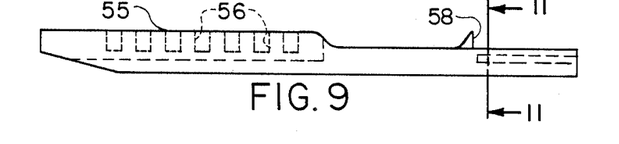
FIG. 9 is a side elevation of the first shaft.
Figure 10:
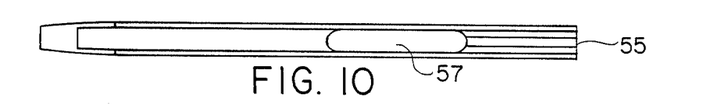
FIG. 10 is a bottom plan of the first shaft.
Figure 11:
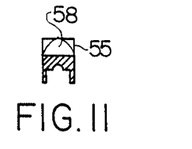
FIG. 11 is a sectional view of the first shaft, taken along the lines 11—11 of FIG. 9.
Figure 12:
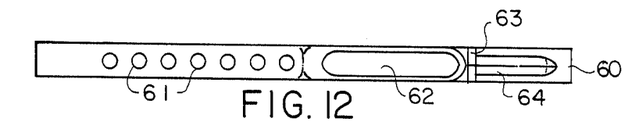
FIG. 12 is a top plan of the second shaft.
Figure 13:
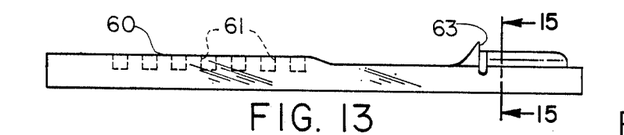
FIG. 13 is a side elevation of the second shaft.
Figure 14:
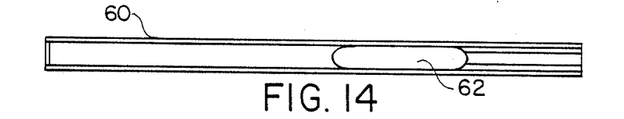
FIG. 14 is a bottom plan of the second shaft.
Figure 15:
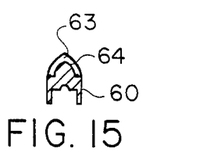
FIG. 15 is a sectional view of the second shaft, taken along the lines 15—15 of FIG. 13.
Figures 16, 17, 19:
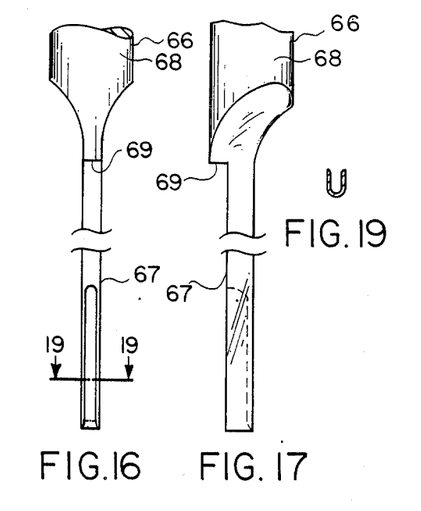
FIG. 16 is a front view of the first chisel.
FIG. 17 is a side view of the first chisel.
FIG. 19 is a sectional view of the first chisel, taken along lines 19—19 of FIG. 16.
Figure 18:
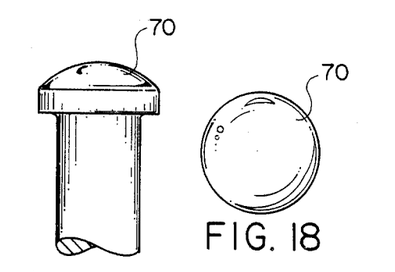
FIG. 18 is a top plan of the first chisel.
Figures 20, 21, 22:
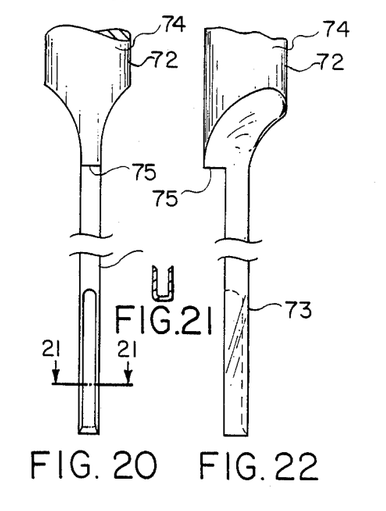
FIG. 20 is a front view of the second chisel.
FIG. 21 is a sectional view of the second chisel, taken along the lines 21—21 of FIG. 20.
FIG. 22 is a side elevation of the second chisel.
Figure 23:
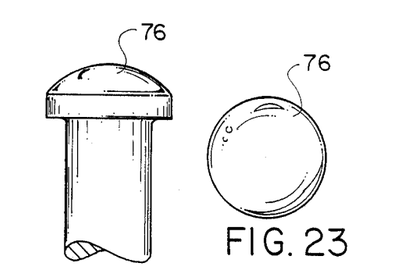
FIG. 23 is a top plan of the second chisel.

FIGS. 6 and 7 show top plan and sectional views, respectively, of the extraction hammer 52. Extraction hammer 52 has a groove 53.

FIGS. 8, 9, 10 and 11 show top, side, bottom and sectional views, respectively, of first shaft 55. First shaft 55 has a plurality of indentations 56 on its top surface as well as an opening 57. There is a stop 58 on the top of first shaft 55. As is seen from FIGS. 10 and 11, first shaft 55 is channeled, or generally "U" shaped in cross section.

FIGS. 12, 13, 14 and 15 show top, side, bottom and sectional views, respectively, of second shaft 60. Second shaft 60 is generally similar in size and shape to first shaft 55. Second shaft 60 has a plurality of indentations 61 on its top surface as well as an opening 62. There is a stop 63 on the top of second shaft 60. There is also an extension 64 on the top of second shaft 60. Like first shaft 55, second shaft 60 is channeled, or generally "U" shaped in cross section.

FIGS. 16, 17, 18 and 19 show front, side, top and sectional views, respectively, of first chisel 66. Blade 67 of first chisel 66 is "U" shaped in cross section. Between blade 67 and shaft 68 of first chisel 66 is a shoulder 69. At the distal end of shaft 68 is a knob 70.

FIGS. 20, 21, 22 and 23 show front, sectional, side and top views, respectively, of second chisel 72. Blade 73 of second chisel 72 is "U" shaped in cross section and is larger than blade 67 of first chisel 66. Second chisel 72 is designed to enlarge the groove in the vertebrae made by first chisel 66. Between blade 73 and shaft 74 of second chisel 72 is a shoulder 75. At the distal end of shaft 74 is a knob 76.

Figure 24:
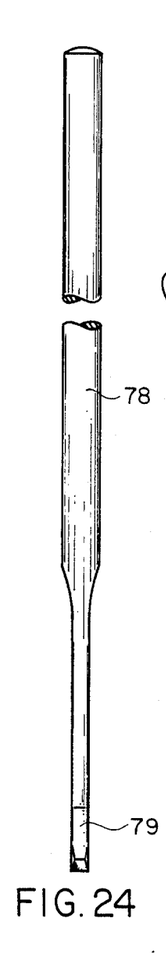
FIG. 24 is a side elevation of the tamper.
Figure 25:
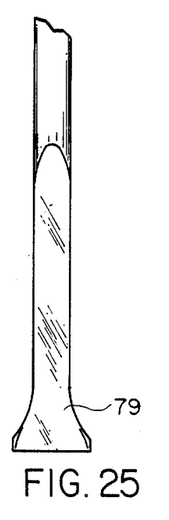
FIG. 25 is a front view of the tamper.
Figure 26:
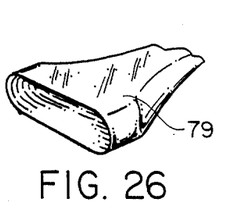
FIG. 26 is an enlarged view of the end portion of the tamper, showing how it is dished to receive the bone graft prior to wedging the bone graft into the groove in the vertebrae.

FIGS. 24 and 25 are side elevation and front view, respectively, of the tamper 78. FIG. 26 is an enlargement of the proximal end 79 of tamper 78 which is dished to accept the bone grafts prior to their being wedged into the grooves of the vertebrae to to fused.

Figure 27:
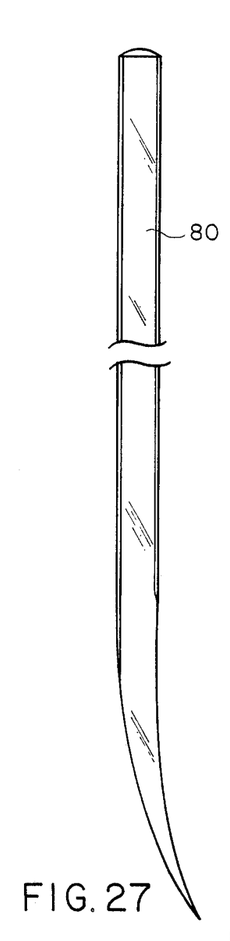
FIG. 27 is a side elevation of the hook.
Figure 28:
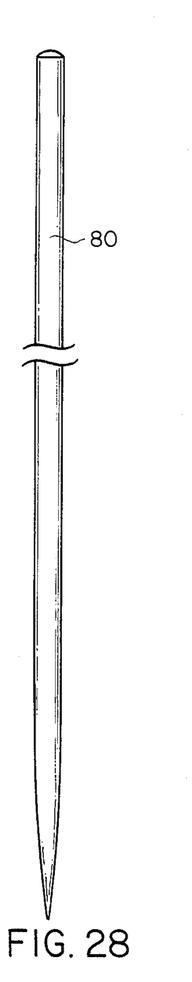
FIG. 28 is a front view of the hook.

FIGS. 27 and 28 show side and front views, respectively, of hook 80.

Figure 29:
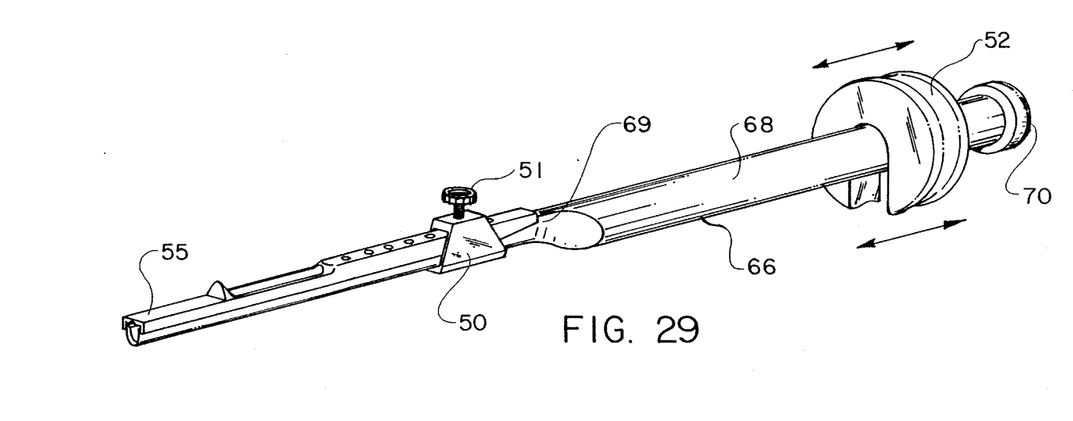
FIG. 29 is a perspective of the first chisel in place in the first shaft, the chisel and shaft being held together by the retaining ring and set screw, and the extraction hammer being shown in place on the chisel.

FIG. 29 shows first chisel 66 inserted in first shaft 55 and held in place with retaining ring 50 and set screw 51. Shoulder 69 on first chisel 66 limits the distance it can be inserted into first shaft 55. Shown on shaft 68 of first chisel 66 is extraction hammer 52 which can be slid up and down shaft 68 of first chisel 66 to strike knob 70 at the distal end of first chisel 66.

The surgical procedure of this invention is carried out as follows. Before operating, it is necessary to establish the site from which the bone graft is to be obtained. Since in the majority of cases, the procedure is carried out on one level, i.e., only two vertebrae are fused, and since the spinal processes are adequate, it is possible to obtain the bone grafts while doing laminectomy. In cases where the spinal processes are too small, or if it is intended to perform bilateral fusion on one or two levels, it is necessary to obtain bone grafts from the posterior iliac crest.

Figure 30:
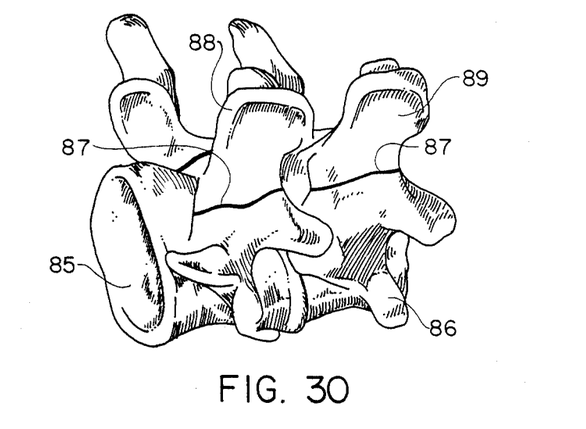
FIG. 30 depicts two lumbar vertebrae with lines indicating the level of laminectomy.
Figure 31:
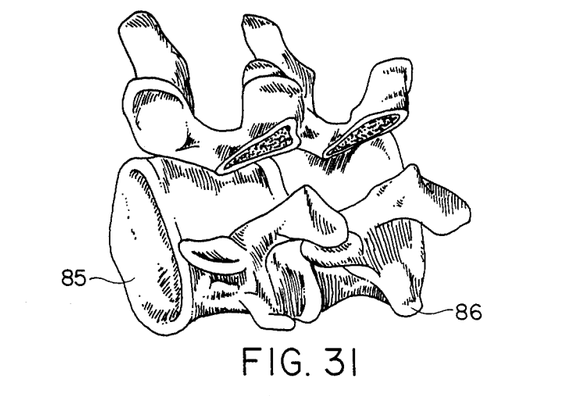
FIG. 31 depicts two lumbar vertebrae after the laminectomy has been performed and the lamina removed.
Figure 32:
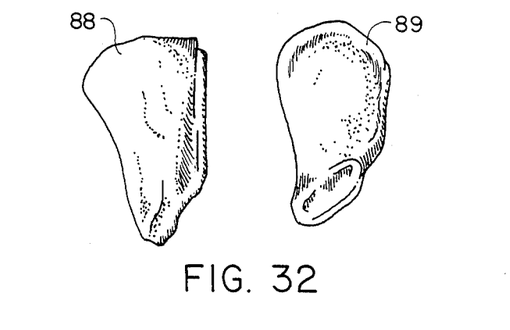
FIG. 32 depicts the lamina after removal from the lumbar vertebrae and prior to shaping for use as bone grafts.

With the patient under general anaesthia and in a prone position, a midline incision is made in the low back. The paravertebral muscles are displaced laterally to expose two levels of vertebrae, usually $L_4$-$L_5$ or $L_5$-$S_1$. In cases of bilateral fusion, lamina are cut at two levels with bone cutters along the spinous process on each side. FIG. 30 shows fourth (upper) lumbar vertebrae 85 and the fifth (lower) lumbar vertebrae 86. Lines 87 indicate the level of laminectomy. Lamine 88 and 89 are removed by laminectomy and are used for the bone grafts. Bone chips are used later for filling up the interbody space. FIG. 31 shows lumbar vertebrae 85 and 86 after laminectomy. FIG. 32 shows lamina 88 and 89 that were removed during laminectomy.

The neural structures are gently displaced medially and any free disk fragments are removed. The interbody space is entered and completely emptied of degenerative disk material. This is done very thoroughly. In cases of bilateral fusion, the interbody space is treated in the same manner also on the opposite side.

Figure 33:
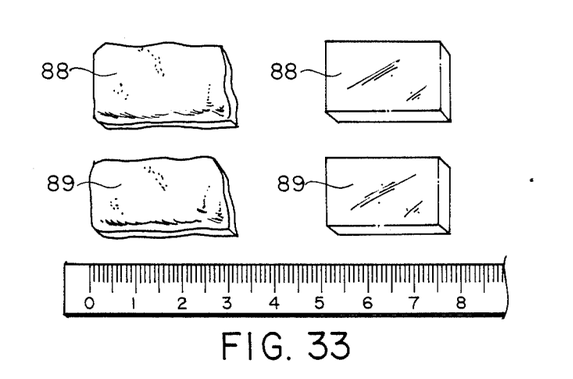
FIG. 33 depicts the lamina shaped for use as bone grafts.

Lamina 88 and 89 are thoroughly cleaned, cartilagineous and fascial elements are removed. The lamina are then shaped into the required dimensions for use as bone grafts, i.e., 14 mm in width, 25 mm-30 mm in height and 4-5 mm in thickness, as shown in FIG. 33.

Figures 34, 35:
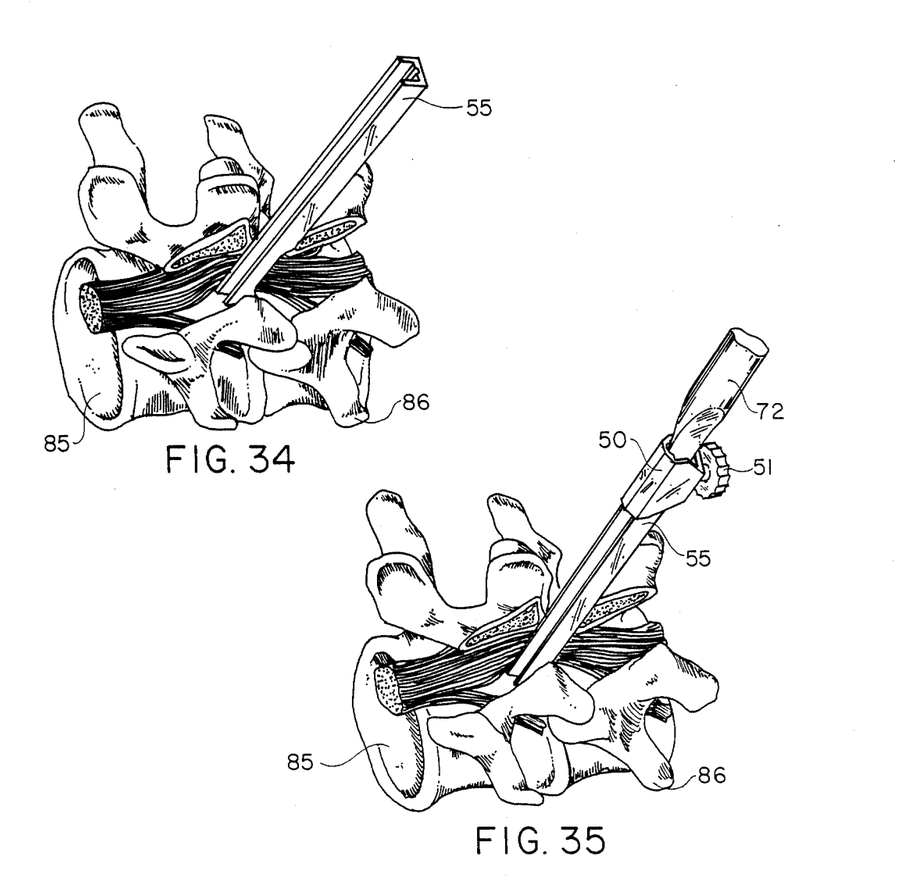
FIG. 34 depicts the first shaft in place in the intervertebral space.
FIG. 35 depicts the first chisel, guided by the first shaft, hammered into the lower edge of the upper vertebrae.

First shaft 55 is then inserted into the intervertebral space as shown in FIG. 35. Stop 58 on the top of the shaft 55 prevents the shaft form slipping through the intervetebral space.

Retaining ring 50 is slid over first shaft 55 and held in place with set screw 51. First chisel 66 is introduced through retaining ring 50 and is guided by first shaft 55. First chisel 66 is checked by shoulder 69 which strikes the end of first shaft 55 and limits passage of first chisel 66 to a depth of 30 mm. In this way a small groove is cut into the cartilagineous and osseous part of the lower edge of upper vertebral body 85, the chips being removed via opening 57. The chisel is removed by sliding the extraction hammer 52 up shank 68 of first chisel 66 so that is strikes knob 70 thereof.

Second chisel 72 is then introduced through retaining ring 50. The depth of second chisel 72 is limited by shoulder 75 striking the end of first shaft 55, as shown in FIG. 35. The groove is deepened, thus insuring osseous contact between the bone grafts and the vertebrae. Second chisel 72 is then removed with the assistance of the hammer 52 and finally first shaft 55 is pulled out from the intervertebral space. Small remaining bone chips in the chisel are removed with hook 80.

Figure 36:
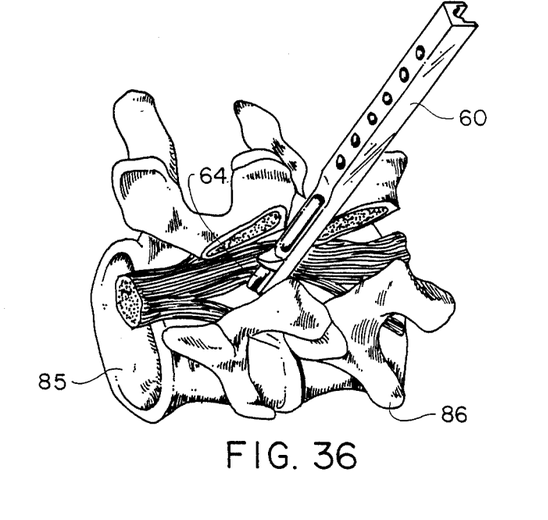
FIG. 36 shows the second shaft in place in the intervertebral space with the extension on the shaft fit into the already-made groove in the upper vertebral body.

Second shaft 60 is then inserted into the intervertebral space with extension 64 fitting snugly into the groove made in the lower edge of the upper vertebral body 85, as shown in FIG. 36.

Figure 37:
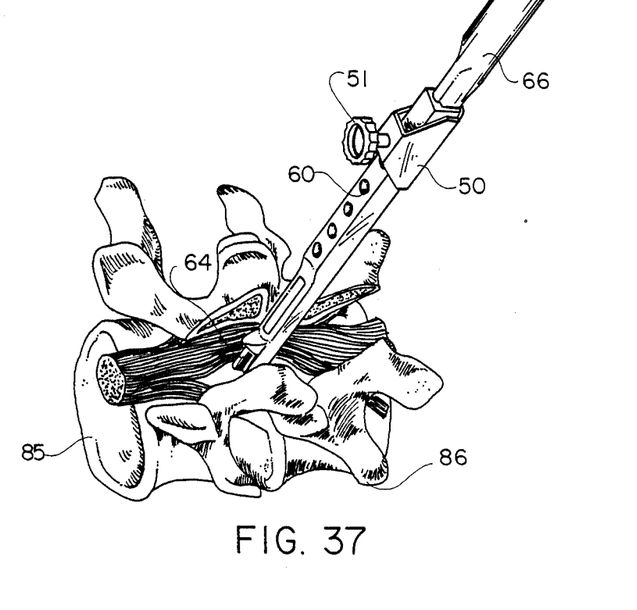
FIG. 37 depicts the second chisel in the second shaft in position to cut the groove into the upper edge of the lower vertebral body.

Retaining ring 50 is slid over shaft 60 and held in place with set screw 51. As described above, first chisel 66 is slid into retaining ring 50 and cuts a small groove into the upper edge of lower vertebrae 86, as shown in FIG. 37. First chisel 66 is removed with the aid of extraction hammer 52, and second chisel 72 is slid into retaining ring 50 to thereby enlarge and deepen the groove made by first chisel 66. Second chisel 72 is removed with the aid of extraction hammer 52, and then second shaft 60 is removed from the intervertebral space.

Figure 38:
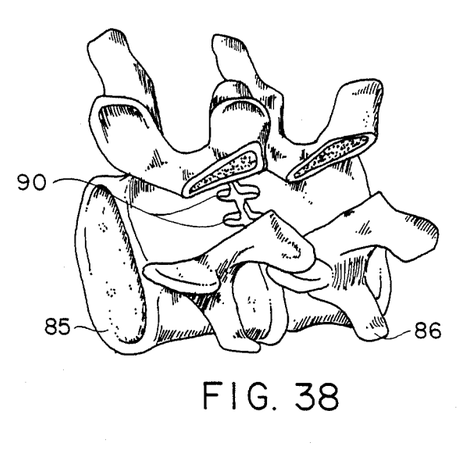
FIG. 38 depicts the two grooves cut in the upper and lower vertebral bodies in a bilateral fusion.

FIG. 38 shows vertebrae 85 and 86 (spinal cord not shown) with two grooves 90 as are required in a bilateral interbody fusion.

Figure 39:
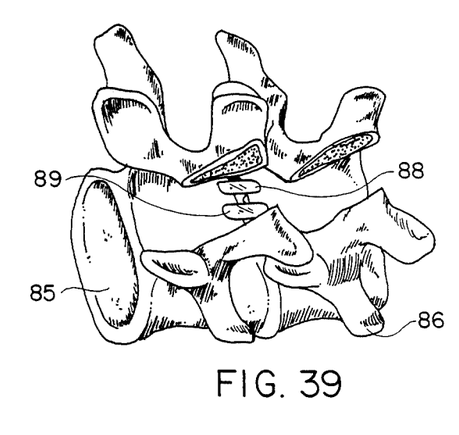
FIG. 39 depicts the bone grafts hammered into place in the interbody space in a bilateral fusion.

As soon as the grooves have been made in vertebrae 85 and 86, prepared bone grafts 88 and 89 are wedged in with the aid of tamper 78 and extraction hammer 52, as shown in FIG. 39. The wound is then closed by suturing the lumbar muscles and fascia.

Thus, the instant invention provides an improved surgical procedure for performing posterior lumbar interbody fusions and an instrument kit for performing the surgery. The surgical procedure is characterized by being faster, less bloody, less expensive and more often successful than traditional surgical procedures. The instrument kit provides surgical instruments that are specifically adapted for use in the procedure of this invention.

While specific embodiments of the present invention have been shown and described in detail to illustrate the utilization of the inventive principles, it is to be understood that such showing and description have been offered only by way of example and not by way of limitation. Protection by Letters Patent of this invention in all its aspects as the same are set forth in the appended claims is sought to the broadest extent that the prior art allows.

What is claimed is:

1. An instrument for cutting a groove in the lower edge of an upper vertebral body to be fused to a lower vertebral body comprising:
    a. a shaft adapted to be inserted into the intervertebral space, the shaft having a back portion with a channel formed therein;
    b. retaining means carried by the shaft; and
    c. a chisel adapted to be slidably received within the channel in the shaft and held therein by the retaining means.

2. The instrument of claim 1, wherein the shaft has a top portion with a protruberance thereon to prevent the shaft from slipping through the intervertebral space.

3. The instrument of claim 1, wherein the chisel has a shoulder which limits the distance the chisel can be slid in the channel of the shaft.

4. The instrument of claim 1, wherein the chisel has a shank with a knob on the end thereof, and wherein an extraction hammer has a groove formed therein for receiving the shank of the chisel, whereby the hammer may be slidably moved along the shank to engage the knob, thereby assisting the removal of the chisel.

5. An instrument for cutting a groove in the upper edge of a lower vertebral body to be fused to an upper vertebral body having a groove already cut in the lower edge thereof comprising:
    a. a shaft adapted to be inserted into the intervertebral space, the shaft having a top surface portion provided with an extension adapted to fit snugly into the groove in the lower edge of the upper vertebral body, and said shaft further having a back portion provided with a channel formed therein;
    b. retaining means carried by the shaft; and
    c. a chisel adapted to be slidably received within the channel in the shaft and held therein by the retaining means.

6. The instrument of claim 5, wherein the shaft has a protruberance on its top to prevent the shaft from slipping through the intervertebral space.

7. The instrument of claim 5, wherein the chisel has a shoulder which limits the distance the chisel can be slid into the channel of the shaft.

8. The instrument of claim 5, wherein the chisel has a shank with a knob on the end thereof, and wherein an extraction hammer has a groove formed therein for receiving the shank of the chisel, whereby the hammer may be slidably moved along the shank to engage the knob, thereby assisting in removal of the chisel.

9. A method for performing a posterior lumbar interbody fusion comprising the steps of:
    a. removing lamina from the two vertebrae to be fused;
    b. cleaning and shaping the lamina for subsequent use as bone grafts;
    c. removing degenerative disk material from between the vertebrae to be fused;
    d. cutting a groove into the lower edge of the upper vertebral body to be fused;

e. cutting a groove into the upper edge of the lower vertical body to be fused, the groove being in line with the groove in the upper vertebral body, and f. wedging a bone graft into the grooves to thereby fuse the upper and lower vertebrae.

10. The method of claim 9, wherein the grooves are cut into the upper and lower vertebrae on one side of the spinal cord and anteriorly thereof.

11. The method of claim 9, wherein the grooves which are cut in the upper and lower vertebrae are fore and aft and are spaced on one side from the midline of the vertebral column to thereby achieve a bilateral fusion.

12. The method of claim 9, wherein the grooves in the upper and lower vertebrae are cut to a depth of about 30 mm.

13. The method of claim 9, wherein the grooves are each shaped and sized to dimensions of about 14 mm by about 25-30 mm by about 4-5 mm.

14. An instrument kit for performing posterior lumbar interbody fusions comprising a first shaft adapted to be inserted into the intervertebral space, the first shaft having a channel means formed therein, a first chisel adapted to be telescopically slidably received within the channel means, shoulder means on the first chisel for limiting the slidable reception of the first chisel within the channel means in the first shaft, means for retaining the first chisel within the channel means in the first shaft, the first shaft having a protuberance thereon for preventing the first shaft from slipping through the intervertebral space, wherein the first chisel is used to cut a small groove into the cartilagineous and osseous part of the lower edge of the upper vertebral body, and wherein the first chisel is thereafter removed from the first shaft, a second chisel thereafter adapted to be telescopically slidably received within the channel means in the first shaft and retained therein, and the second chisel having shoulder means thereon for limiting the distance the second chisel may be slidably received within the respective channel means in the first shaft, wherein the second chisel is used to deepen the groove, thereby assuring osseous contact between the vertebrae and subsequent bone grafts.

15. The kit of claim 14, further including a second shaft adapted to be inserted into the intervertebral space after the first shaft has been removed, the second shaft having aportion adapted to fit snugly into the groove in the lower edge of the upper vertebral body, the second shaft having a respective channel means formed therein, and the second shaft having a protuberance formed thereon to prevent the second shaft from slipping through the intervertebral space, wherein the second shaft is inserted into the groove made in the lower edge of the upper vertebral body, wherein the first chisel is thereafter received within the second shaft to cut a small groove in the upper edge of the lower vertebrae, and wherein after the first chisel is removed, the second chisel is received within the second shaft to enlarge and deepen the groove made by the first chisel in the upper edge of the lower vertebrae.

16. The kit of claim 14, wherein the retaining means comprises a retaining ring adapted to straddle the respective first shaft and first chisel, and a set screw carried by the retaining ring.

17. The kit of claim 14, further including a hammer member having a slot formed therein for receiving the shank of the first chisel, the first chisel having a knob on the end thereof, whereby the hammer member may be slid along the shank of the chisel to engage the knob thereon.

18. The kit of claim 14, further including a tamper having a shank and further having a lower end dished to accept bone grafts, whereby the tamper may be used for wedging the bone grafts into the grooves to thereby fuse the upper and lower vertebrae.

* * * * *